US012622869B2

(12) United States Patent
Denkinger et al.

(10) Patent No.: US 12,622,869 B2
(45) Date of Patent: May 12, 2026

(54) LIPID EMULSION FOR PARENTERAL ADMINISTRATION

(71) Applicant: Fresenius Kabi Deutschland GmbH, Bad Homburg (DE)

(72) Inventors: Melanie Denkinger, Oberursel (DE); Ewald Schlotzer, Bad Homburg (DE); Edmundo Brito De La Fuente, Bad Homburg (DE); Lida A. Quinchia-Bustamante, Friedberg (DE); Crispulo Gallegos-Montes, Bad Homburg (DE)

(73) Assignee: FRESENIUS KABI DEUTSCHLAND GMBH, Bad Homburg (DE)

( * ) Notice: Subject to any disclaimer, the term of this patent is extended or adjusted under 35 U.S.C. 154(b) by 312 days.

(21) Appl. No.: 17/257,229

(22) PCT Filed: Jul. 1, 2019

(86) PCT No.: PCT/EP2019/067511
§ 371 (c)(1),
(2) Date: Dec. 30, 2020

(87) PCT Pub. No.: WO2020/007758
PCT Pub. Date: Jan. 9, 2020

(65) Prior Publication Data
US 2021/0290526 A1      Sep. 23, 2021

(30) Foreign Application Priority Data

Jul. 3, 2018    (EP) ..................................... 18181432

(51) Int. Cl.

| | |
|---|---|
| *A61K 9/00* | (2006.01) |
| *A61K 9/107* | (2006.01) |
| *A61K 31/14* | (2006.01) |
| *A61K 31/197* | (2006.01) |
| *A61K 31/202* | (2006.01) |
| *A61K 31/355* | (2006.01) |
| *A61K 31/575* | (2006.01) |
| *A61K 35/60* | (2006.01) |
| *A61K 36/06* | (2006.01) |
| *A61K 36/48* | (2006.01) |
| *A61K 36/63* | (2006.01) |
| *A61P 1/16* | (2006.01) |
| *A61P 29/00* | (2006.01) |

(52) U.S. Cl.
CPC ............ *A61K 9/0029* (2013.01); *A61K 9/107* (2013.01); *A61K 31/14* (2013.01); *A61K 31/197* (2013.01); *A61K 31/202* (2013.01); *A61K 31/355* (2013.01); *A61K 31/575* (2013.01); *A61K 35/60* (2013.01); *A61K 36/06* (2013.01); *A61K 36/48* (2013.01); *A61K 36/63* (2013.01); *A61P 1/16* (2018.01); *A61P 29/00* (2018.01)

(58) Field of Classification Search
None
See application file for complete search history.

(56) References Cited

U.S. PATENT DOCUMENTS

2014/0030377 A1      1/2014  Arterbum et al.

FOREIGN PATENT DOCUMENTS

| | | | | |
|---|---|---|---|---|
| CN | 1965806 A | 5/2007 | | |
| KR | 20150052084 A | 5/2015 | | |
| WO | WO 2016188876 A1 * | 1/2016 | | |
| WO | WO-2016040570 A2 * | 3/2016 | ............. | A23L 29/10 |
| WO | 2016156528 A1 | 10/2016 | | |

OTHER PUBLICATIONS

Goulet et al., A new intravenous fat emulsion containing soybean oil, medium-chain triglycerides, olive oil, and fish oil: a single-center, double-blind randomized study on efficacy and safety in pediatric patients receiving home parenteral nutrition, 2010, JPEN, 34: 485-95.*
Mauro et al., Beneficial effects of docosahexaenoic acid on cognition in age-related cognitive decline, 2010, Alzheimer's & Dementia, 6: 456-464.*
Burrin et al., "Impact of New-Generation Lipid Emulsions on Cellular Mechanisms or Parenteral Nutrition-Associated Lived Disease," Advances in Nutrition, 5(1), Jan. 1, 2014, 82-91.
Goulet et al., "A New Intravenous Fat Emulsion Containing Soybean Oil, Medium-Chain Triglycerides, Olive Oil, and Fish Oil," Sep. 17, 2010, Journal of Parenteral and Enteral Nutrition, 34(5), 485-495.
Smoflipid Product Information, 2016, FDA.
Yurko-Mauro et al., "Beneficial effects of docoshexaenoic acid on cognition in age-related cognitive decline," May 3, 2010.
European Patent Office, CN 1965806 A, Patent Translate.
European Patent Office, KR 20150052084 A, Patent Translate.

* cited by examiner

*Primary Examiner* — Anand U Desai
*Assistant Examiner* — Catheryne Chen
(74) *Attorney, Agent, or Firm* — HYLTON-RODIC LAW PLLC

(57) ABSTRACT

The present disclosure relates to lipid emulsions for parenteral administration, comprising 10 to 30% of a lipid phase comprising soybean oil, medium-chain triglycerides (MCT), olive oil and fish oil and less than 25 mg, preferably less than 20 mg, campesterol, less than 30 mg, preferably less than 25 mg, stigmasterol and less than 120 mg, preferably less than 100 mg, betasitosterol per 100 g of the lipid phase. The present disclosure also relates to the lipid emulsions according to the present disclosure for providing parenteral nutrition, in particular to neonates, as well as to methods for manufacturing the lipid emulsions according to the present disclosure.

19 Claims, No Drawings

LIPID EMULSION FOR PARENTERAL ADMINISTRATION

CROSS REFERENCE TO RELATED APPLICATIONS

This application is a U.S. national stage application of International Application No. PCT/EP2019/067511, filed Jul. 1, 2019, which claims the benefit of the filing date of European Application 18181432.8, filed Jul. 3, 2018, the contents of which are hereby incorporated by reference in their entirety.

FIELD OF THE INVENTION

The present disclosure relates to lipid emulsions for parenteral administration, particularly for use in providing parenteral nutrition.

BACKGROUND OF THE INVENTION

Lipid emulsions for parenteral administration have been used clinically for nutritional and medical purposes for several years. Lipid emulsions comprising soybean or safflower oil were first introduced more than 50 years ago.

Parenteral nutrition (PN) is prescribed as exclusive PN regimen or as PN complementary to enteral nutrition (EN) when oral or EN is impossible, contraindicated, or insufficient.

Preterm infants, especially extremely low birth weight preterm infants and preterm infants of early gestational age, are usually on parenteral nutrition as part of their routine care during the first weeks of life as their gastrointestinal tract is not yet mature enough to tolerate, digest and assimilate breast milk or infant formula.

Extremely low birth weight infants are at increased risk of poor growth and development and prone to develop morbidities and dysfunctions both short and long term.

For many years the standard of care for preterm infants has been the parenteral administration of soybean and/or olive oil based lipid emulsions along with amino acid and glucose solutions. However, the fatty acid profile of these plant oil based lipid emulsions is very different from the provision in utero or that of human breast milk which may be considered to have the most appropriate composition.

The administration of the above mentioned soybean and/or olive oil based commercial lipid emulsions has in many cases led to e.g. profound alterations in fatty acid status, fat accumulation in the liver, or parenteral nutrition associated liver disease (PNALD), particularly in neonates and preterm infants. Furthermore, it is assumed that neonatal morbidities such as e.g. late-onset sepsis and chronic lung disease may—at least in part—be related to the fatty acid profiles of these emulsions.

Also, the plant oils comprised in commercial lipid emulsions are naturally rich in phytosteroles. Phytosteroles, however, have been controversially discussed as a contributing factor for the development of liver dysfunction and cholestasis, and it would thus be desirable to provide lipid emulsions with lower phytosterole content.

Hence there is the need for lipid emulsions for parenteral nutrition at least partially overcoming the above mentioned drawbacks, particularly for lipid emulsions tailored to the needs of premature neonates.

SUMMARY OF THE INVENTION

The present disclosure relates to lipid emulsions for parenteral administration. The lipid emulsions according to the present disclosure comprise 10 to 30% of a lipid phase. The lipid phase comprises soybean oil, medium-chain triglycerides (MCT), olive oil and fish oil and less than 25 mg, preferably less than 20 mg, campesterol, less than 30 mg, preferably less than 25 mg, stigmasterol and less than 120 mg, preferably less than 100 mg, beta-sitosterol per 100 g of the lipid phase. Preferably, the lipid phase comprises less than 0.2 wt. %, preferably less than 0.15 wt. % total phytosteroles based on the total weight of this lipid phase.

The present disclosure also relates to the lipid emulsions according to the present disclosure for providing parenteral nutrition, in particular to neonates, as well as to methods for manufacturing the lipid emulsions according to the present disclosure.

DETAILED DESCRIPTION OF THE INVENTION

The present disclosure relates to lipid emulsions for parenteral administration. The lipid emulsions according to the present disclosure are oil-in-water emulsions, i.e. the continuous phase is aqueous and comprises oil droplets. The emulsions according to the present disclosure comprise the continuous aqueous phase and preferably 10% to 30% of a lipid phase based on the total volume of the emulsion (w/v). For example, the emulsions comprise 10%, 20% or 30% of a lipid phase based on the total volume of the emulsion (w/v).

More preferably, the emulsions comprise 20% of a lipid phase based on the total volume of the emulsion (w/v). The aqueous phase comprises water in purity suitable for parenteral administration, i.e. water for injection.

Oil-in-water emulsions for parenteral administration have to be sterile, pyrogen-free, well tolerated, free of particulate impurities and storage stable.

The Lipid Phase

The lipid phase comprises soybean oil, olive oil, fish oil and medium chain triglycerides (MCT). Preferably, the lipid phase comprises 20 to 40 wt. %, preferably 25 to 35 wt. % soybean oil, 20 to 40 wt. %, preferably 25 to 35 wt. %, MCT, 15 to 35 wt. %, preferably 20 to 30 wt. %, olive oil and 1 to 20 wt. %, preferably 2 to 8 wt. % fish oil based on the total weight of the lipid phase. For the sake of clarity it is to be understood that the sum of these ingredients does not exceed 100%.

The lipid phase comprises less than 25 mg, preferably less than 20 mg, campesterol, less than 30 mg, preferably less than 25 mg stigmasterol and less than 120 mg, preferably less than 100 mg, beta-sitosterol per 100 g of the lipid phase. Preferably, the lipid phase comprises less than 0.2 wt. %, preferably less than 0.15 wt. %, total phytosteroles based on the total weight of the lipid phase.

In a preferred embodiment of the present disclosure the lipid phase further comprises 1 to 10 wt. %, preferably 2 to 6 wt. % arachidonic acid based on the total weight of the lipid phase. Preferably, the arachidonic acid is provided by adding a fungal oil to the lipid phase. Preferably, the fungal oil is derived from *Mortierella alpina*. Preferably, the fungal oil comprises at least 20 wt. %, preferably at least 30 wt. %, more preferably at least 40 wt. % arachidonic acid based on the total weight of the fungal oil.

Hence, in another preferred embodiment of the present disclosure the lipid phase comprises 20 to 40 wt. %, preferably 25 to 35 wt. % soybean oil, 20 to 40 wt. %, preferably 25 to 35 wt. %, MCT, 15 to 35 wt. %, preferably 20 to 30 wt. %, olive oil, 1 to 15 wt. %, preferably 2 to 8 wt. % fish oil and 2 to 20 wt. %, preferably 5 to 15 wt. % fungal oil based on the total weight of the lipid phase.

The term "fish oil" refers to "purified fish oil" and to "purified fish oil rich in omega 3 fatty acids", the latter according to the European Pharmacopoeia 6.0 comprising at least 9% (w/w) of the omega-3-fatty acid docosahexaenoic acid (DHA) and at least 13% (w/w) of the omega-3 fatty acid eicosapentaenoic acid (EPA) expressed as triglycerides.

In the context of the present disclosure the term "fish oil" also refers to fish oil extracts that may be further enriched or downgraded respectively in certain fatty acids. Such fish oil extracts are commercially available, e.g. from Solutex S.L.

The term "eicosapentaenoic acid (EPA) triglycerides" as used herein refers to triglycerides comprising (5Z,8Z,11Z,14Z,17Z)-5,8,11,14,17-icosapentaenoic acid, also known as 20:5(n-3). EPA is a an omega-3 fatty acid with a 20-carbon chain and five cis double bonds; the first double bond is located at the third carbon from the omega end.

The term "docosahexaenoic acid (DHA) triglycerides" as used herein refers to triglycerides comprising all-cis-docosa-4,7,10,13,16,19-hexa-enoic acid, also known as 22:6(n-3). DHA is an omega-3 fatty acid that is a primary structural component of the human brain, cerebral cortex, skin, sperm, testicles and retina. Docosahexaenoic acid is a 22-carbon chain with six cis double bonds, the first double bond being located at the third carbon from the omega end.

The EPA and DHA triglycerides may be obtained by any way known to those skilled in the art.

It is known that docosahexaenoic acid (DHA) and eicosapentaenoic acid (EPA) and the derivatives thereof are contained per se, or in the form of glycerides and in the form of other derivatives, in natural fats and oils, particularly in fats and oils of aquatic animals (e.g., fish, marine mammals, and crustaceans such as krill and other euphausiids), animal tissues (e.g., brain, liver, eyes, etc.) and animal products such as eggs or milk.

Thus, for example, they may be extracted from animal sources including aquatic animals (e.g., fish, marine mammals, and crustaceans such as krill and other euphausiids), animal tissues (e.g., brain, liver, eyes, etc.) and/or animal products such as eggs or milk.

Some methods for the isolation of these docosahexaenoic acid (DHA) and eicosapentaenoic acid (EPA) and their derivatives and their conversion to pure docosahexaenoic acid (DHA) triglycerides and eicosapentaenoic acid (EPA) triglycerides are described in the art.

Such isolation by purification can be achieved by any means known to those of skill in the art and can include the extraction, e.g. by supercritical fluid extraction, of an oil from an organism which produces DHA and/or EPA and the subsequent purification via chromatographic methods. Alternatively, the oils can be extracted using extraction techniques such as are described in U.S. Pat. No. 6,750,048. Additional extraction and/or purification techniques are taught e.g. in WO2001/076715 and WO2001/076385.

In a preferred embodiment of the present disclosure the fish oil comprises DHA triglycerides and EPA triglycerides in a weight ratio of from 10:1 to 6:1, preferably of from 10:1 to 7:1, more preferably of from 9:1 to 8:1. Preferably, the fish oil comprises at least 50 wt. %, preferably at least 60 wt. %, more preferably at least 70 wt. % omega-3 fatty acids based on the total weight of the fish oil.

Hence, in a preferred embodiment of the present disclosure the lipid phase comprises 1 to 10 wt. %, preferably 2 to 5 wt. % DHA based on the total weight of the lipid phase.

In another preferred embodiment the lipid phase comprises less than 5 wt. %, preferably less than 3 wt. %, more preferably less than 2 wt. % EPA based on the total weight of the lipid phase.

The term "medium chain triglycerides" refers to triglycerides of fatty acids having 6 to 12 carbon atoms in length, including caproic acid, caprylic acid, capric acid and lauric acid.

The oil phase preferably comprises n-6 and n-3 fatty acids in a weight ratio of from 7:1 to 2:1, preferably of from 6:1 to 3:1, more preferably of from 4.5:1 to 3.5:1.

The Emulsifier

The emulsions according to the present disclosure comprise at least one pharmaceutically acceptable emulsifier. The term "emulsifier" refers to compounds which stabilize the composition by reducing the interfacial tension between the oil phase and the water phase and which typically comprise at least one hydrophobic group and at least one hydrophilic group. These emulsifiers (which may also be referred to as surfactants) are preferably used in amounts effective to provide, optionally together with further surfactants present, a stable and even distribution of the oil phase within the aqueous phase. In particular, the emulsifier is selected from the group of emulsifiers that have been approved for parenteral administration.

Preferably, the at least one emulsifier is a phospholipid. Within the meaning of the present disclosure the term "phospholipids" refers to naturally occurring or synthetic phospholipids that may be suitably refined. Suitable phospholipids include, but are not limited to, phospholipids derived from corn, soybean, egg or other animal origin, or mixtures thereof. Phospholipids typically comprise mixtures of diglycerides of fatty acids linked to the choline ester of phosphoric acid and can contain differing amounts of other compounds depending on the method of isolation. Typically, commercial phospholipids are a mixture of acetone-insoluble phosphatides. Preferably, the phospholipids are obtained from egg or other animal origin, or from seeds including soybean and corn, using methods well known in the art. Phospholipids obtained from soybean are referred to herein as soy phospholipids. Phospholipids obtained from egg are referred to herein as egg phospholipids.

Preferably, the emulsions comprise phospholipids as emulsifier, more preferably the phospholipids are selected from the group consisting of egg phospholipids, soy phospholipids, and mixtures thereof.

These are commercially available, e.g. under the trade names Epikurin™170 (soy phospholipids), PL 90 or Lipoid E80 (both egg phospholipids).

Preferably, the phospholipids are used in an amount of 0.5 to 5% (w/v), more preferably 0.5 to 3% (w/v), most preferably 1.0 to 2.0% (w/v).

The Antioxidant

The emulsion may comprise at least one pharmaceutically acceptable antioxidant.

An antioxidant useful in the emulsion of the disclosure may be any pharmaceutically acceptable compound having antioxidant activity, for example, the antioxidant may be selected form the group consisting of sodium metasulfite, sodium bisulfite, sodium sulfite, sodium thiosulfate, thioglycerol, thiosorbitol, thioglycolic acid, cysteine hydrochloride, n-acetyl-cysteine, citric acid, alpha-tocopherol, beta-tocopherol, gamma-tocopherol, delta-tocopherol, tocotrienols, soluble forms of vitamin E, butylated hydroxyanisole (BHA), butylated hydroxytoluene (BHT), t-butylhydroquinone (TBHQ), monothioglycerol, propyl gallate, histidine, enzymes such as superoxide dismutase, catalase, selenium glutathione peroxidase, phospholipid hydroperoxide and glutathione peroxidase, Coenzyme Q10, carotenoids, quinones, bioflavonoids, polyphenols, bilirubin, ascorbic acid, isoascorbic acid, uric acid, metal-binding proteins, ascorbic acid palmitate, and mixtures thereof.

The at least one antioxidant is in particular selected from the group consisting of alpha-tocopherol, beta-tocopherol, gamma-tocopherol, delta-tocopherol, tocotrienols, ascorbic acid, and mixtures of two or more thereof. Preferably, the antioxidant is alpha-tocopherol.

If present, the total amount of agents with antioxidant activity is preferably in the range of from 0.01% to 0.05%, more preferably from 0.01% to 0.04%, more preferably from 0.01% to 0.03%, and even more preferably from 0.015% to 0.025% based on the total volume of the emulsion (w/v).

The Tonicity Agent

The emulsion may comprise at least one pharmaceutically acceptable tonicity agent. Tonicity agents are used to confer tonicity. Suitable tonicity agents may be selected from the group consisting of sodium chloride, mannitol, lactose, dextrose, sorbitol and glycerol. Preferably, the tonicity agent is glycerol.

Preferably, the total amount of tonicity agents is in the range of 0.1 to 10%, more preferably from 1% to 5%, more preferably from 1% to 4%, more preferably 1% to 3%, more preferably from 1.5% to 2.8%, and even more preferably from 2.0% to 2.5% based on the total volume of the emulsion (w/v).

In case the tonicity agent is glycerol the most preferred amount is 2.0% to 2.4% based on the total volume of the emulsion (w/v).

Preferably, the emulsion has an osmolality in the range of 305 to 450 mOsmol/kg.

pH Adjustment

The pH of the lipid emulsions may be adjusted by adding solutions of conventionally known acids or bases such as HCl and NaOH or through the use of buffers, such as phosphate buffers.

The final pH of the emulsion is preferably in the range of from 6 to 9, more preferably between 7 and 9.

Preferably, the pH of the emulsion according to the disclosure is adjusted using a solution of NaOH.

The Co-Surfactant

The lipid emulsions according to the disclosure may further comprise a pharmaceutically acceptable co-surfactant.

A co-surfactant is an amphiphilic molecule, i.e. a molecule that contains both hydrophilic and lipophilic groups. Usually, a co-surfactant substantially accumulates with the emulsifier at the interfacial layer. The hydrophile-lipophile balance (HLB) number is used as a measure of the ratio of hydrophilic and lipophilic groups present in a surfactant or co-surfactant, respectively. Usually, a co-surfactant with a very low HLB value (thus with a relatively high affinity to oil) is used together with a surfactant with a high HLB to modify the overall HLB of the system. Unlike the emulsifier, the co-surfactant may not be capable of forming self-associated structures, like micelles, on its own. Several kinds of molecules including nonionic emulsifiers, alcohols, amines and acids, can function as co-surfactants in a given system.

The co-surfactant is usually used in a lower amount than that of the emulsifier. Apart from modifying the overall HLB value of the system, the co-surfactant has the effect of further reducing the interfacial tension and increasing the fluidity of the interface. Co-surfactants may also adjust the curvature of the interfacial film by partitioning between the tails of the emulsifier chains, allowing greater penetration of the oil between the emulsifier tails.

Preferably, the co-surfactant is a free long chain fatty acid or a salt thereof, preferably a free unsaturated fatty acid or a salt thereof, preferably an omega-9 fatty acid or a salt thereof, more preferably a monounsaturated omega-9 fatty acid or a salt thereof, more preferably oleic acid.

The total amount of the co-surfactant is preferably in the range of from 0.01% to 1%, more preferably in the range of from 0.02% to 0.5%, more preferably in the range of from 0.02% to 0.2% based on the total volume of the emulsion (w/v).

Further Ingredients

The lipid emulsions according to the present disclosure may comprise further additives.

In a preferred embodiment of the present disclosure, the lipid emulsions further comprise L-carnitine or a salt or derivative thereof and/or choline or a salt or derivative thereof. Preferably, the lipid emulsions comprise both L-carnitine or a salt or derivative thereof and choline or a salt or derivative thereof.

Preferably, choline is provided in form of cytidine 5'-diphosphocholine sodium, choline chloride or alpha-glyceryl phosphoryl choline. Preferably, the lipid emulsions according to the present disclosure comprise choline at a concentration of 1 to 2 g per litre, preferably at a concentration of 1.1 to 1.7 g per litre based on the total volume of the emulsion.

Preferably, L-carnitine is provided in free form. Preferably, the lipid emulsions according to the present disclosure comprise L-carnitine at a concentration of 500 to 1500 mg per litre, preferably at a concentration of 600 to 1000 mg per litre based on the total volume of the emulsion.

The Droplet Size

Since the lipid emulsions of the disclosure are oil-in-water emulsions, the continuous phase is aqueous and comprises oil droplets. These oil droplets are stabilized within the aqueous phase by at least one emulsifier and optionally further additives. The size of the oil droplets depends on the qualitative and quantitative composition of the emulsion and its preparation.

The oil droplets of the emulsion herein preferably have a mean diameter of 130 to 450 nm, preferably 150 to 400 nm, more preferably 180 to 350 nm, when measured directly upon sterilization using an LS 13 320 Laser Diffraction Particle Size Analyser (Beckman Coulter) according to USP <729>.

Preparation of the Lipid Emulsion

The present disclosure also relates to a method for preparing the lipid emulsions according to the present disclosure, wherein the method comprises a) providing an oil phase comprising soybean oil, medium-chain triglycerides, olive oil, and fish oil and optionally a pharmaceutically acceptable antioxidant and/or a pharmaceutically acceptable co-surfactant, b) providing an aqueous phase comprising water for injection, a pharmaceutically acceptable emulsifier and optionally a pharmaceutically acceptable tonicity agent and/or an agent for pH adjustment, c) forming a pre-emulsion by mixing the oil phase provided in step a) with the aqueous phase provided in step b), d) forming the emulsion by high-pressure homogenizing the pre-emulsion obtained in step c) and e) sterilising the emulsion obtained in step d), wherein optionally the emulsion is filled into a suitable container before or after sterilization.

It is to be understood that any of the optional further components of the emulsion may be added in any of the steps a), b), c) or d) or in one or more additional steps.

Step a)

Step a) is preferably carried out by mixing olive oil, soybean oil, fish oil, MCT and optionally a fungal oil and/or a pharmaceutically acceptable antioxidant and/or a pharmaceutically acceptable co-surfactant. This step is preferably carried out at a temperature of 55 to 75° C. ° C., until a homogeneous and clear phase is obtained.

It is to be understood that in step a) further additives may be added.

In particular, it is to be understood that the at least one pharmaceutically acceptable emulsifier—depending on its nature—may be added either in step a) or in step b).

Step b)

Step b) is preferably carried out by providing water for injection and optionally adding a pharmaceutically acceptable tonicity agent.

The aqueous phase is then heated to a temperature of 55 to 75° C., preferably to 60 to 70° C.

It is to be understood that in step b) further additives may be added.

In particular, it is to be understood that the at least one pharmaceutically acceptable emulsifier—depending on its nature—may be added either in step a) or in step b).

Preferably, the emulsifier is a phospholipid and is added in step b), more preferably after the aqueous phase has been heated to 55 to 75° C.

Step c)

The method further comprises mixing the oil phase provided in step a) with the aqueous phase provided in step b) thereby forming a pre-emulsion. The mixing may be carried out by any method known to those skilled in the art.

Preferably the oil phase is added to the aqueous phase or vice-versa at a temperature in the range of from 55 to 75° C., more preferably at a temperature between 6° and 70° C.

It is to be understood that further components may also be added after the formation of the pre-emulsion. According to a preferred embodiment, the pH of the pre-emulsion may be adjusted to a pH in the range of from 7 to 9, in particular by adding sodium hydroxide, if necessary.

Step d)

The method further comprises the homogenization of the pre-emulsion obtained in step c). This homogenization may be carried out by any suitable method known to those skilled in the art.

Preferably the mixture is homogenized at a temperature in the range of from 40 to 60° C., more preferably at a temperature between 45 and 55° C.

Preferably, the pre-emulsion is homogenized in a two-step homogenizer in a number of passages.

Preferably the pH of the emulsion is adjusted after the homogenization step.

The pH is adjusted to values between 7 and 9, preferably to values between 8 and 9.

Step e)

The method further comprises the sterilization of the emulsion obtained in step d) to ensure its suitability for parenteral administration.

The sterilization may be carried out by any suitable method known to those skilled in the art. In particular, the sterilization is carried out by autoclaving, preferably at a temperature in the range of from 119 to 122° C., more preferably at a temperature around 121° C., preferably for a time in the range of from 1 minute to 30 minutes, preferably of from 10 minutes to 15 minutes.

Route of Administration

The lipid emulsions according to the present disclosure are adapted for parenteral administration, i.e. for a route of administration "other than via the gastrointestinal tract". Preferably, the compositions according to the present disclosure are administered intravenously, either into a peripheral or a central vein.

Lipid emulsions for parenteral administration have to be sterile, pyrogen-free, well tolerated, free of particulate impurities and storage stable. Their pH should be as close as possible to the pH of the blood.

Use of the Lipid Emulsions

The lipid emulsions according to the present disclosures may be used to provide parenteral nutrition, preferably to pediatric patients. Preferably, the pediatric patients are neonates, more preferably preterm infants. The preterm infants may have a birthweight of below 2500 g, of below 2200 g, of below 2000 g, of below 1900 g, of below 1800 g, of below 1700 g, of below 1600 g, of below 1500 g, of below 1400 g, of below 1300 g, of below 1200 g, of below 1100 g, or of below 1000 g.

In preterm infants the lipid emulsions according to the present invention are administered in daily doses of 1 to 4 g lipid per kg body weight for providing total parenteral nutrition (TPN). If the lipid emulsion comprises 20% (w/v) lipids this corresponds to daily doses of 5 to 20 ml lipid emulsion per kg bodyweight.

It is to be understood that the initial doses may be low (e.g. 5 ml per kg bodyweight per day) and may gradually be increased (to e.g. 15 to 20 ml per kg bodyweight per day) and that the doses may have to be adapted depending on nutrient uptake via other than the parenteral route, e.g. that the dose will have to be decreased if an infant is additionally fed an infant formula and/or breastfed.

In pediatric patients, particularly in neonates and preterm infants, the lipid emulsions according to the present disclosure support neurodevelopment, and/or neurocognitive development and improve intestinal morphology and/or growth and/or body composition. Furthermore, they support neurological functions, immune response, mitochondrial function, gut flora, liver function and bile flow. They are also useful for the resolution of inflammation and they improve nutrient utilization. They may also be used in the prevention or treatment of sepsis, chronic lung disease, cachexia, liver fat accumulation, parenteral nutrition associated liver disease, inflammatory diseases, necrotizing enterocolitis, retinopathy or bronchopulmonary dysplasia.

While the lipid emulsions according to the present disclosure are particularly useful in providing parenteral nutrition to preterm infants, they may also be used to provide total or partial parenteral nutrition to adults, e.g. to intensive care patients, critically ill patients, metabolically stressed patients, short bowel or intestinal failure patients, immunodeficient patients, cancer patients, cachexia patients and/or malnourished patients.

In adults the lipid emulsions according to the present invention are usually administered in daily doses of 1 to 2 g lipid per kg body weight for providing total parenteral nutrition (TPN). If the lipid emulsion comprises 20% (w/v) lipids this corresponds to daily doses of 5 to 10 ml lipid emulsion per kg bodyweight.

It is to be understood that the dose may have to be adapted depending on nutrient uptake via other than the parenteral route, e.g. that the dose will have to be decreased if the patient additionally receives enteral nutrition.

In adults the lipid emulsions according to the present disclosure support neurological functions, immune response, mitochondrial function, gut flora, liver function and bile flow. They may also be used for the resolution of inflammation and to improve nutrient utilization. Further, they may be used in the prevention or treatment of sepsis, chronic lung disease, cachexia, liver fat accumulation, parenteral nutrition associated liver disease or inflammatory diseases.

For example the lipid emulsions according to the present disclosure may be used in the treatment or prevention of cachexia in cancer patients, of sepsis in critically ill patients, of liver fat accumulation in metabolically stressed patients, or of parenteral nutrition associated liver disease in patients with short bowel syndrome or intestinal failure. They may also be used to support immune response in critically ill patients, to support immune response in cancer patients, to support immune response in immunodeficient patients, to support gut flora in metabolically stressed patients and to improve nutrient utilization in malnourished patients.

Embodiments

1) Lipid emulsion for parenteral administration comprising an aqueous phase and 10 to 30% of a lipid phase based on the total volume of the emulsion (w/v), wherein the lipid phase comprises soybean oil, medium-chain triglycerides, olive oil, and fish oil, and wherein the lipid phase comprises less than 25 mg, preferably less than 20 mg, campesterol, less than 30 mg, preferably less than 25 mg stigmasterol and less than 120 mg, preferably less than 100 mg, beta-sitosterol per 100 g of the lipid phase.

2) Lipid emulsion according to embodiment 1, wherein the lipid phase comprises less than 0.2 wt. %, preferably less than 0.17 wt. %, more preferably less than 0.15 wt. %, total phytosteroles based on the total weight of the lipid phase.

3) Lipid emulsion according to embodiment 1 or 2 for use as a medicament.

4) Lipid emulsion for use according to embodiment 1, 2 or 3 for providing parenteral nutrition to a subject in need thereof.

5) Lipid emulsion for use according to embodiment 4, wherein the subject is a pediatric patient, preferably a neonate, more preferably a preterm infant.

6) Lipid emulsion for use according to embodiment 5 for supporting neurodevelopment and/or neurocognitive development and/or neurological functions and/or immune response and/or mitochondrial function and/or gut flora and/or liver function and/or bile flow and/or for the resolution of inflammation and/or for improving intestinal morphology and/or growth and/or body composition and/or nutrient utilization.

7) Lipid emulsion for use according to embodiment 4, wherein the subject is an adult patient, e.g. an intensive care patient, a critically ill patient, a short bowel patient, an intestinal failure patient, a metabolically stressed patient, an immunodeficient patient, a cancer patient, a cachexia patient and/or a malnourished patient.

8) Lipid emulsion for use according to embodiment 7 for supporting neurological functions, immune response, mitochondrial function, gut flora, liver function, bile flow and/or resolution of inflammation and/or for improving intestinal morphology and/or nutrient utilization.

9) Lipid emulsion according to any of embodiments 1 or 2 or for use according to embodiment 3 to 8 for use in the treatment or prevention of sepsis, chronic lung disease, cachexia, liver fat accumulation, parenteral nutrition associated liver disease, inflammatory diseases, necrotizing enterocolitis, retinopathy or bronchopulmonary dysplasia.

10) Use of a lipid emulsion according to embodiment 1 or 2 for providing parenteral nutrition to a subject in need thereof.

11) Use according to embodiment 10, wherein the subject is a pediatric patient, preferably a neonate, more preferably a preterm infant.

12) Use according to embodiment 11 for supporting neurodevelopment and/or neurocognitive development and/or neurological functions and/or immune response and/or mitochondrial function and/or gut flora and/or liver function and/or bile flow and/or for the resolution of inflammation and/or for improving intestinal morphology and/or growth and/or body composition and/or nutrient utilisation.

13) Use according to embodiment 10, wherein the subject is an adult patient, e.g. an intensive care patient, a critically ill patient, a short bowel patient, an intestinal failure patient, a metabolically stressed patient, an immunodeficient patient, a cancer patient, a cachexia patient and/or a malnourished patient.

14) Use according to embodiment 13 for supporting neurological functions, immune response, mitochondrial function, gut flora, liver function, bile flow and/or resolution of inflammation and/or for improving intestinal morphology and/or nutrient utilisation.

15) Lipid emulsion according to embodiment 1 or 2, wherein the fish oil comprises at least 35 wt. % DHA based on the total weight of the fish oil.

16) Lipid emulsion according to any of the embodiments 1, 2 or 15, wherein the fish oil comprises less than 10 wt. % EPA based on the total weight of the fish oil.

17) Lipid emulsion according to any of the embodiments 1, 2, 15 or 16, wherein the lipid phase further comprises at least 1 wt. %, preferably at least 2 wt. % arachidonic acid based on the total weight of the lipid phase.

18) Lipid emulsion according to embodiment 17, wherein arachidonic acid is provided by adding a fungal oil to the lipid phase.

19) Lipid emulsion according to embodiment 18, wherein the fungal oil comprises at least 20 wt. %, preferably at least 30 wt. % arachidonic acid based on the total weight of the fungal oil.

20) Lipid emulsion according to any of the embodiments 1, 2 or 15 to 19, wherein the lipid phase comprises 20 to 40 wt. %, preferably 25 to 35 wt. %, soybean oil, 20 to 40 wt. %, preferably 25 to 35 wt. %, medium-chain triglycerides, 15 to 35 wt. %, preferably 20 to 30 wt. %, olive oil, 1 to 15 wt. %, preferably 2 to 8 wt. %, fish oil and 2 to 20 wt. %, preferably 5 to 15 wt. %, fungal oil based on the total weight of the lipid phase.

21) Lipid emulsion according to embodiment 18 or 19, wherein the fungal oil is derived from *Mortierella alpina*.

22) Lipid emulsion according to any of the embodiments 1, 2 or 15 to 21 comprising 1-10 wt., preferably 2-5 wt. % DHA based on the total weight of the lipid phase.

23) Lipid emulsion according to any of the embodiments 1, 2 or 15 to 22 comprising 1-10 wt. %, preferably 2-6 wt. % arachidonic acid based on the total weight of the lipid phase.

24) Lipid emulsion according to any of the embodiments 1, 2 or 15 to 23 comprising less than 5 wt. %, preferably less than 3 wt. %, more preferably less than 2 wt. % EPA based on the total weight of the lipid phase.

25) Lipid emulsion according to any of the embodiments 1, 2 or 15 to 24 further comprising choline or a salt or derivative thereof and/or L-carnitine or a salt or derivative thereof.

26) Lipid emulsion according to any of the embodiments 1, 2 or 15 to 25 further comprising alpha-tocopherole or a derivative thereof.

27) Use of a lipid emulsion according to any of the embodiments 15 to 26 for providing parenteral nutrition to a subject in need thereof.

28) Use according to embodiment 27, wherein the subject is a pediatric patient, preferably a neonate, more preferably a preterm infant.

29) Use according to embodiment 27, wherein the subject is an adult patient, e.g. an intensive care patient, a critically ill patient, a short bowel patient, an intestinal failure patient, a metabolically stressed patient, an immunodeficient patient, a cancer patient, a cachexia patient and/or a malnourished patient.

30) Use according to embodiment 28 for supporting neurodevelopment and/or neurocognitive development and/or for improving growth and/or body composition.

31) Use according to any of embodiments 27 to 29 for supporting neurological functions, immune response, mitochondrial function, gut flora, liver function, bile flow and/or resolution of inflammation and/or for improving intestinal morphology, growth, body composition and/or nutrient utilization.

32) Lipid emulsion according to any of embodiments 15 to 26 for use as a medicament.

33) Lipid emulsion according to any of embodiments 15 to 26 or for use according to embodiment 31 for providing parenteral nutrition to a subject in need thereof.

34) Lipid emulsion for use according to embodiment 33, wherein the subject is a pediatric patient, preferably a neonate, more preferably a preterm infant.

35) Lipid emulsion for use according to embodiment 33, wherein the subject is an adult patient, e.g. an intensive care patient, a critically ill patient, a short bowel patient, an intestinal failure patient, a metabolically stressed patient, an immunodeficient patient, a cancer patient, a cachexia patient and/or a malnourished patient.

36) Lipid emulsion for use according to embodiment 34 for supporting neurodevelopment and/or neurocognitive development and/or for improving growth and/or body composition.

37) Lipid emulsion for use according to any of embodiments 33 to 35 for supporting neurological functions, immune response, mitochondrial function, gut flora, liver function, bile flow and/or resolution of inflammation and/or for improving intestinal morphology and/or nutrient utilisation.

38) Lipid emulsion according to any of embodiments 1, 2 and 15 to 26 or for use according to any of embodiments 32 to 37 for use in the treatment or prevention of sepsis, chronic lung disease, cachexia, liver fat accumulation, parenteral nutrition associated liver disease, inflammatory diseases retinopathy or bronchopulmonary dysplasia.

39) Method for preparing a lipid emulsion according to any of embodiments 1, 2 and 15 to 26 comprising
   a) providing an oil phase comprising soybean oil, medium-chain triglycerides, olive oil, and fish oil and optionally a pharmaceutically acceptable antioxidant and/or a pharmaceutically acceptable co-surfactant,
   b) providing an aqueous phase comprising water for injection, a pharmaceutically acceptable emulsifier and optionally a pharmaceutically acceptable tonicity agent and/or an agent for pH adjustment,
   c) forming a pre-emulsion by mixing the oil phase provided in step a) with the aqueous phase provided in step b),
   d) forming the emulsion by high-pressure homogenizing the pre-emulsion obtained in step c) and
   e) sterilising the emulsion obtained in step d), wherein optionally the emulsion is filled into a suitable container before or after sterilisation.

40) Method according to embodiment 39, wherein the antioxidant comprised in the oil phase provided in step a) is alpha-tocopherol.

41) Method according to embodiment 39 or 40, wherein the co-surfactant comprised in the oil phase provided in step a) is a free long chain fatty acid, preferably oleic acid.

42) Method according to any of embodiments 39 to 41, wherein the emulsifier comprised in the aqueous phase provided in step b) is a phospholipid, preferably egg yolk lecithin.

43) Method according to any of embodiments 39 to 42, wherein the aqueous phase provided in step b) is heated to a temperature of 55° C. to 75° C., preferably to a temperature of 60° C. to 70° C., before the surfactant is added.

44) Method according to any of embodiments 39 to 43, wherein step c) is conducted at a temperature of 55° C. to 75° C., preferably at a temperature of 60° C. to 70° C.

45) Method according to any of embodiments 39 to 44, wherein step d) is conducted at a temperature of 40° C. to 60° C., preferably at a temperature of 45° C. to 55° C.

46) Method according to any of embodiments 39 to 45, wherein after step d) and prior to step e) the pH of the emulsion is adjusted to values between 7 and 9, preferably to values between 8 and 9, preferably by adding a pharmaceutically acceptable base, preferably a solution of NaOH.

EXAMPLES

Example 1

The lipid emulsion comprises the following ingredients in the following amounts:

| Lipid emulsion 20% | Quantity |
| --- | --- |
| Soy-bean oil, refined | 60 g |
| medium-chain triglycerides (MCT) | 60 g |
| Olive oil, refined | 50 g |
| Fungal oil (Denk, article no. 971447) | 20 g |

-continued

| Lipid emulsion 20% | Quantity |
| --- | --- |
| Fish oil extract (Solutex, 0063TG) | 10 g |
| all-rac-alpha-Tocopherol | 190 mg |
| Purified egg phospholipids (PL90) | 12 g |
| Glycerol, anhydrous | 22.5 g |
| Oleic acid | 1 g |
| Sodium hydroxide | to pH approx. 8.5 |
| Water for injections | to 1000 ml |
| Nitrogen | |

The lipid emulsion was prepared according to the following process:

Soybean oil, medium chain triglycerides, olive oil, fungal oil, fish oil extract, alpha-tocopherol and oleic acid were mixed and heated to 60 to 70° C.

Glycerol and water for injection were mixed and heated to 60 to 70° C. and then egg phospholipids were added under continuous stirring.

The oil phase and the water phase were mixed under vigorous stirring at 60 to 70° C., and the pH was adjusted by adding a solution of sodium hydroxide.

The pre-emulsion was then homogenised in a two-step homogeniser in 6 passages at a pressure of 500/50 bar. The temperature was maintained between 45 and 55° C. during the homogenisation.

After the homogenisation the emulsion was cooled to below 30° C. and the pH was adjusted to approximately 8.5.

Finally, the emulsion was sterilized by autoclaving at 121° C.

The emulsion was stored at 25° C. and at 40° C. respectively and found to be stable for at least 12 months.

Example 2

The lipid emulsion according to example 1 was administered to premature piglets and compared to the commercial lipid emulsion Intralipid® 20% in the following experimental setup:

Premature pigs were delivered 6 days preterm at 108 days gestation from pregnant sows by caesarean section. Maternal plasma (16 ml/kg intravenously for the first 24 hours) was administered to the pigs for passive immunological protection to compensate for the lack of colostrum. Pigs were treated every other day with prophylactic antibiotics (ampicillin, 50 mg/kg, intravenously) to prevent catheter related infections. Preterm pigs were implanted with central vein catheters and given total parenteral nutrition (TPN) solutions (lipid emulsion plus an elemental nutrition solution containing amino acids, glucose, electrolytes, vitamins and trace elements) continuously starting at a rate of 5 ml fluid per kg per hour. Within the following 6 study days the rate of infusion was gradually increased to 10 ml per kg per hour and maintained for the remaining days. Group 1 received Intralipid® 20% and group 2 received the emulsion according to example 1. The 2 groups received the same amounts of glucose, amino acids and total lipids. The only difference between the groups was the composition of the lipid emulsion.

On day 20 pigs were subjected to body composition analysis. On day 22, all pigs were euthanized for plasma/serum and tissue collection and analysis. Contents from the small intestine and the colon were also collected.

Example 2a) Fatty Acid Content in Red Blood Cells, Liver and Brain

Red blood cells, liver and brain tissue were analysed for total fatty acid composition using GC-MS. On day 22 red blood cells and liver of pigs in group 2 contained significantly more DHA than those of the pigs in group 1. Also, DHA concentration in the frontal cortex was higher in group 2 than in group 1. These results indicate sufficient bioavailability of DHA from the emulsion according to the disclosure.

| DHA (mg/100 g tissue) | Group 1 | Group 2 |
| --- | --- | --- |
| liver | 45.1 +/− 3.61 | 113 +/− 9.10 |
| red blood cells | 5.71 +/− 0.38 | 12.1 +/− 0.80 |
| frontal cortex | 105 +/− 7.1 | 130 +/− 13.7 |

Example 2b) Body Composition and Liver Weight

On day 20 pigs were briefly anaesthetized with an anaesthetic combination of tiletamine and zolazepam (2.2 mg/kg Telazol®) mixed with xylazine (1.1 mg/kg XylaMed™) and their body composition was determined by dual-energy X-ray absorptiometry (DXA) using a fan-beam densitometer (Hologic QDR4500A) in the infant whole body scan mode. Scan results provided values for total body bone mineral content (BMC), bone mineral density (BMD), non-bone lean tissue, and total body fat mass. Summing BMC and lean tissue values provided a measure of fat-free mass (FFM).

The pigs in group 1 were found to have a higher percent body fat mass than the pigs in group 2 (8.03+/−0.38% in group 1 versus 5.41+/−0.43% in group 2).

Also, on day 22, the livers of the pigs in group were lighter than the livers of the pigs in group 1, indicating a reduction of hepatomegaly often observed during long-term parenteral nutrition (59.5+/−1.89 g/kg bodyweight in group 1 versus 47.7+/−1.42 g/kg body weight in group 2).

Example 2c) Markers of Insulin Resistance

| | Group 1 | Group 2 |
| --- | --- | --- |
| Serum glucose (μmol/L) | 98.3 +/− 10.1 | 101 +/− 10.8 |
| Plasma insulin (pmol/L) | 101 +/− 18.7 | 33.6 +/− 6.02 |
| HOMA-IR | 3.8 +/− 0.9 | 1.4 +/− 0.9 |

Insulin and glucose were measured in plasma samples after 22 days and HOMA-IR was calculated. Both insulin and HOMA-IR were found to be significantly lower in group 2 than in group 1, indicative of prevention of insulin resistance associated with standard soybean oil emulsions.

Example 2d) TNF-Alpha Expression in Hippocampus and Frontal Cortex

Brain tissues were assayed by qRT-PCR for mRNA of TNF-alpha. The relative quantification of target mRNA expression was calculated and normalized to beta-actin expression using the 2-$\Delta\Delta$CT method.

TNF-alpha expression was found to be more than 2-fold higher in group 1 than in group 2 both in the hippocampus and in the frontal cortex, indicative of prevention of inflammatory activity in the brain.

Example 2e) GGT, Bilirubin, Total Bile Acids, FGF19, Cholesterol

GGT, direct bilirubin, bile acids, FGF19, phytosterols and cholesterol were measured on day 22 in plasma or serum respectively. Bile acid concentrations were also measured in the contents of the small intestine and the colon.

|  | Group 1 | Group 2 |
|---|---|---|
| Serum GGT (U/L) | 228.0 +/− 41.2 | 56.5 +/− 10.3 |
| Serum direct bilirubin (mg/dl) | 0.84 +/− 0.14 | 0.17 +/− 0.03 |
| Total plasma bile acids (µmol/L) | 42.1 +/− 4.9 | 7.9 +/− 1.2 |
| Total bile acids in contents of the small intestine (µmol) | 6.5 +/− 2.3 | 41.9 +/− 7.8 |
| Total bile acids in contents of the colon (µmol) | 9.1 +/− 1.7 | 37.4 +/− 8.3 |
| Total plasma cholesterol (µmol/L) | 625.0 +/− 21.6 | 515.0 +/− 38.6 |
| Total plasma phytosterols (µmol/L) | 84.0 +/− 3.0 | 26.8 +/− 2.4 |

Serum GGT, serum direct bilirubin and total plasma bile acid, cholesterol and phytosterol levels were significantly lower in group 2 than in group 1, suggesting improved liver function, bile flow and protection against cholestasis.

Plasma FGF19 was found to be considerably lower in group 1 (352.4+/−54.2 pg/ml) than in group 2 (602.2+/−96.6 pg/ml)—together with the enhanced bile acid concentrations in the small intestine and colon—indicative of an improved bile flow in group 2.

Example 2f) Distal Ileum Morphometry

Tissue sections of the small intestine (proximal jejunum and distal ileum) were fixed in 10% buffered formalin for 24 hours. Morphometric analysis was performed in H&E stained and Alcian Blue stained tissue sections. Villus height, crypt depth and goblet cell numbers were assessed. Villus height and crypt depth were found to be significantly bigger in the pigs of group 2 suggesting an improvement of mucosal growth in group 2 as compared to group 1.

|  | Group 1 | Group 2 |
|---|---|---|
| Villus height (µm) | 331 +/− 23 | 434 +/− 25 |
| Crypt depth (µm) | 117 +/− 3 | 140 +/− 4 |

Example 2g) Colonic Microbiome Analysis

Colon contents were collected and processed for amplicon sequencing of the V4 region of the 16S ribosomal RNA gene. The PowerSoil isolation kit (Mo Bio Laboratories) was used to extract genomic DNA, followed by PCR amplification of the V4 region of the bacterial 16S rRNA gene and sequencing using the 2×250 paired-end protocol on an Illumina MiSeq.

The number of operational taxonomic units (OTU) and the inverse Simpson values (InvSimpson) were assessed. OTU is an operational definition used to classify groups of closely related bacterial species based on the sequence of 16S ribosomal RNA genes and a rough approximation for number of bacterial species. The InvSimpson is a similar parameter that measures the degree of diversity among bacterial species and corrects for the relative abundance of each OTU.

Both the OTU and InvSimpson values were significantly lower in group 2 than in group 1. Further phylogenetic classification of bacteria at the class level showed lower abundances of Clostridia, Bacilli and Negativicutes and increased Gammaproteobacteria in group 2 than in group 1.

Further analysis at the genus level showed increased Enterobacteriaceae and decreased *Clostridium* XIVa in group 2 as compared to group 1.

Example 2h) Colonic Metabolomics Analysis

The faeces of the piglets were subjected to metabolic profiling. The samples were prepared using the automated MicroLab STAR® system (Hamilton). To remove protein, small molecules bound to protein or trapped in the precipitated protein matrix were dissociated, and to recover chemically diverse metabolites, proteins were precipitated with methanol under vigorous shaking for 2 minutes followed by centrifugation. The resulting extract was analysed by ultra-high performance liquid chromatography-tandem mass spectroscopy (UPLC-MS/MS).

The faeces of the piglets in group 2 contained markedly more carnitine derivatives of fatty acids than the faeces of the piglets in group 1, indicative of an increased bioavailability and metabolism of fatty acids in group 2.

Further, the faeces of the piglets in group 2 contained markedly less arachidonic acid and more 9- and 13-hydroxyoctadecadienoic acid (9- and 13-HODE) than faeces of the piglets in group 1, predictive of reduced inflammatory activity in group 2.

Also, a significant accumulation of mead acid (20:3n9) was detected in the faeces of the piglets of group 1 but not in the faeces of the piglets in group 2. An increase of mead acid has been attributed to a deficiency in essential fatty acids.

The invention claimed is:

1. A lipid emulsion for parenteral administration comprising an aqueous phase and 10 to 30% of a lipid phase based on the total volume of the emulsion (w/v),
   wherein the lipid phase comprises 20 wt. % to 40 wt. % soybean oil, 20 wt. % to 40 wt. % medium-chain triglycerides, 15 wt. % to 35 wt. % olive oil, and 1-15 wt. % fish oil extract,
   wherein the lipid phase comprises less than 25 mg campesterol, less than 30 mg stigmasterol and less than 120 mg beta-sitosterol per 100 g of the lipid phase,
   wherein the lipid phase further comprises 1 to 10 wt. % arachidonic acid based on the total weight of the lipid phase,
   wherein the arachidonic acid is provided by adding a fungal oil to the lipid phase,
   wherein the lipid phase comprises 2 to 20 wt. % fungal oil based on the total weight of the lipid phase,
   wherein the fish oil extract comprises both DHA and EPA, and
   wherein said DHA is present in an amount of at least 35 wt. % and said EPA is present in an amount of less than 10 wt. % based on the total weight of the fish oil extract.

2. The lipid emulsion according to claim 1, wherein the lipid phase comprises less than 0.2 wt. % total phytosterols based on the total weight of the lipid phase.

3. The lipid emulsion according to claim 1, wherein the emulsion comprises at least 1-10 wt. % DHA and less than 3 wt. % EPA based on the total weight of the lipid phase.

4. The lipid emulsion according to claim 1, wherein the lipid phase comprises 2 wt. % to 6 wt. % arachidonic acid based on the total weight of the lipid phase.

5. The lipid emulsion according to claim 1, wherein the lipid phase comprises 25 wt. % to 35 wt. %, soybean oil, 25 wt. % to 35 wt. % medium-chain triglycerides, 20 wt. % to 30 wt. % olive oil, 2 wt. % to 8 wt. % fish oil and 5 wt. % to 15 wt. % fungal oil based on the total weight of the lipid phase.

6. The lipid emulsion according to claim 4, wherein the fungal oil is derived from *Mortierella alpina*.

7. The lipid emulsion according to claim 3, said emulsion comprising 1-10 wt. % DHA and less than 5 wt. % EPA based on the total weight of the lipid phase.

8. The lipid emulsion according to claim 1, wherein the fungal oil comprises at least 20 wt. % arachidonic acid based on the total weight of the fungal oil.

9. The lipid emulsion according to claim 4, said emulsion further comprising alpha-tocopherol or a derivative thereof.

10. A medicament, said medicament comprising a lipid emulsion according to claim 1.

11. A method for providing parenteral nutrition to a subject in need thereof, said method comprising administering a lipid emulsion of claim 1 to said subject.

12. The method according to claim 11, wherein the subject is a pediatric patient.

13. The method according to claim 11, wherein the subject is an adult patient.

14. A method for supporting neurodevelopment and/or neurocognitive development and/or for improving growth and/or body composition, said method comprising administering a lipid emulsion of claim 1 to a pediatric patient in need thereof.

15. A method supporting neurological functions, immune response, mitochondrial function, gut flora, liver function, bile flow and/or resolution of inflammation and/or for improving intestinal morphology and/or nutrient utilization, said method comprising administering a lipid emulsion of claim 1 to a subject in need thereof.

16. A method for use in the treatment of sepsis, chronic lung disease, cachexia, liver fat accumulation, parenteral nutrition associated liver disease, inflammatory diseases, retinopathy or bronchopulmonary dysplasia, said method comprising administering a lipid emulsion of claim 1 to a subject in need thereof.

17. A method for preparing a lipid emulsion, said method comprising
  a) providing an oil phase comprising soybean oil, medium-chain triglycerides, olive oil, and fish oil and optionally a pharmaceutically acceptable antioxidant, preferably alpha-tocopherol and/or a pharmaceutically acceptable co-surfactant,
  b) providing an aqueous phase comprising water for injection, a pharmaceutically acceptable emulsifier, and optionally a pharmaceutically acceptable tonicity agent and/or an agent for pH adjustment,
  c) forming a pre-emulsion by mixing the oil phase provided in step a) with the aqueous phase provided in step b);
  d) forming the emulsion by high-pressure homogenizing the pre-emulsion obtained in step c) and
  e) sterilising the emulsion obtained in step d), wherein optionally the emulsion is filled into a suitable container before or after sterilization.

18. The method according to claim 17, wherein the aqueous phase provided in step b) is heated to a temperature of 55° C. to 75° C., before the surfactant is added and/or wherein step c) is conducted at a temperature of 55° C. to 75° C.

19. The method according claim 17, wherein step d) is conducted at a temperature of 40° C. to 60° C.

\* \* \* \* \*